(12) United States Patent
Schechterman

(10) Patent No.: US 7,405,877 B1
(45) Date of Patent: Jul. 29, 2008

(54) STEREOSCOPIC ENDOSCOPE

(75) Inventor: Mark Schechterman, Nes-Ziona (IL)

(73) Assignee: Visionsense Ltd., Petah Tikva (IL)

( * ) Notice: Subject to any disclaimer, the term of this patent is extended or adjusted under 35 U.S.C. 154(b) by 729 days.

(21) Appl. No.: 10/364,053

(22) Filed: Feb. 10, 2003

(51) Int. Cl.
  *G02B 27/26* (2006.01)
  *G02B 27/22* (2006.01)

(52) U.S. Cl. .................. 359/465; 359/462; 359/464

(58) Field of Classification Search ........... 359/465, 359/462, 352, 495, 498, 464; 353/8; 348/43, 348/49, 57; 600/111, 101, 166
See application file for complete search history.

(56) References Cited

U.S. PATENT DOCUMENTS

| 5,121,983 | A | * | 6/1992 | Lee ................. 353/8 |
| 5,471,237 | A | | 11/1995 | Shipp |
| 5,527,263 | A | | 6/1996 | Zobel et al. |
| 5,689,365 | A | | 11/1997 | Takahashi |
| 5,743,846 | A | | 4/1998 | Takahashi et al. |
| 5,912,762 | A | * | 6/1999 | Li et al. ............. 359/352 |
| 6,075,555 | A | * | 6/2000 | Street ............. 348/43 |
| 6,154,315 | A | | 11/2000 | Street |

\* cited by examiner

*Primary Examiner*—Audrey Y Chang
(74) *Attorney, Agent, or Firm*—Merchant & Gould P.C.

(57) ABSTRACT

Stereoscopic device, including a first image detector and a second image detector, a first entrance pupil, receiving a first image of an object, a second entrance pupil, receiving a second image the object, a directional image separator, receiving the first and second images from the respective first and second entrance pupils, a common optical imaging assembly, located between the entrance pupil and the directional image separator, conveying the images from the respective entrance pupils to the directional image separator, providing the first image to the directional image separator in a first source direction, and providing the second image to the directional image separator in a second source direction, wherein the directional image separator includes a directionally selective surface, the directionally selective surface reflecting the first image in a first target direction, towards the first image detector, and transmitting the second image in a second target direction, towards the second image detector, and wherein the first image and the second image are at least partially overlapping, when arriving at the directionally selective surface.

10 Claims, 4 Drawing Sheets

STEREOSCOPIC ENDOSCOPE

FIELD OF THE DISCLOSED TECHNIQUE

The disclosed technique relates to stereoscopic endoscopes, in general, and to methods and systems for stereoscopic image pick-up devices with color imaging capability, in particular.

BACKGROUND OF THE DISCLOSED TECHNIQUE

Stereoscopic image detection devices are known in the art. When such devices are used for Minimum Invasive Surgery (MIS) applications, it is desirable to obtain a combination of minimal shaft cross-section and high image quality.

Stereoscopic endoscopes are typically characterized, at least partially, by separate optical channels. Each such channel provides separate ray tracing from the object toward human eyes or photoelectric sensors. Another type of conventional stereoscopic endoscopes uses a common optical system, while the optical channels are separated using time division, or according to light polarization direction.

Production tolerances and separate adjustment of each optical channel in a conventional stereoscopic endoscope may cause different optical characteristics of each optical channel, namely different magnification, focusing, off-set and tilt. This makes the requirement of high image quality more difficult to achieve.

U.S. Pat. No. 5,471,237 issued to Shipp, and entitled "Single Lens Stereoscopic Video Camera", is directed to a stereoscopic video camera system, which uses a single objective lens system mounted at the distal end of a surgical endoscope. According to one embodiment, the camera is used to provide images of an object located near the distal end of an endoscope, from two different eye perspectives. The endoscope includes a single objective lens system and an electronic shutter. The electronic shutter includes left and right optical zones, each capable of assuming an opaque state and a transmissive state. A drive signal causes one zone to become opaque while the other is transmissive, and vice versa.

U.S. Pat. No. 5,527,263 issued to Zobel et al., and entitled "Stereo Endoscope", is directed to a stereo endoscope. The shaft of the stereo endoscope includes two optical systems, arranged in close proximity to each other, and a housing, located on the proximal end of the shaft. A stereo optical device connects at the proximal end of the optical systems, thereby providing a stereo view into the optical system.

U.S. Pat. No. 5,689,365 issued to Takahashi et al., and entitled "Stereoscopic-Vision Endoscope", is directed to a stereoscopic endoscope. The endoscope includes a main optical system having a single optical axis, and a rotary optical system having right and left optical axes. An object is illuminated, thereby providing a left image and a right image to the main optical system, with a parallax difference there between.

U.S. Pat. No. 5,743,846 issued to Takahashi et al., and entitled "Stereoscopic Endoscope Objective Lens System Having a Plurality of Front Lens Groups and One Common Rear Lens Group", is directed to a stereoscopic endoscope. Two images, having a parallax from each other, are formed by two respective objective optical systems, in spatially separated positions. The images are transmitted by a relay optical system, and separately formed on a photoelectrically converting surface of an image taking device.

U.S. Pat. No. 6,154,315 issued to Street, and entitled "Apparatus and Method for Stereoscopic Endoscopy", is directed to a stereoscopic endoscope. The endoscope comprises a birefringent slab of calcite, an objective lens assembly, a relay system, a lens, a reflecting prism, a polarizing beam splitter, a lens and two CCD arrays.

Light from two points in an object field travels through the birefringent slab, before reaching a entrance pupil of the optical system. The birefringent slab affects the light, when viewed from the object field, in a manner equivalent the endoscope presenting two displaced entrance pupils. The polarizing beam splitter transmits light having one polarization direction, to one of the CCD arrays, and reflects light having an orthogonal polarization direction, to the second CCD array.

SUMMARY OF THE DISCLOSED TECHNIQUE

It is an object of the disclosed technique to provide a novel method and system for stereoscopic imaging using common optical imaging assembly. Directional image separator reflects one of the images toward one of the detectors and transmit second image toward second detector. The presented method overcomes the disadvantages of the prior art.

In accordance with the disclosed technique, there is thus provided a stereoscopic device, which includes a common optical imaging assembly and a directional image separator, based on optical layers with coefficient of reflection depending on angle of incidence. Rays with small angle of incidence are reflected and rays with large angle of incidence are transmitted.

In accordance with the disclosed technique, there is thus provided a stereoscopic device, which includes a common optical imaging assembly and a directional image separator, based on optical layers with coefficient of reflection depending on angle of incidence. Rays with small angle of incidence are transmitted and rays with large angle of incidence are reflected.

In accordance with the disclosed technique, there is thus provided a stereoscopic device, which includes a common optical imaging assembly and a directional image separator, based on Total Internal Reflection (TIR) principle. Rays with small angle of incidence are transmitted and rays with large angle of incidence are reflected.

BRIEF DESCRIPTION OF THE DRAWINGS

The disclosed technique will be understood and appreciated more fully from the following detailed description taken in conjunction with the drawings, in which.

DETAILED DESCRIPTION OF THE EMBODIMENTS

Figure 1:
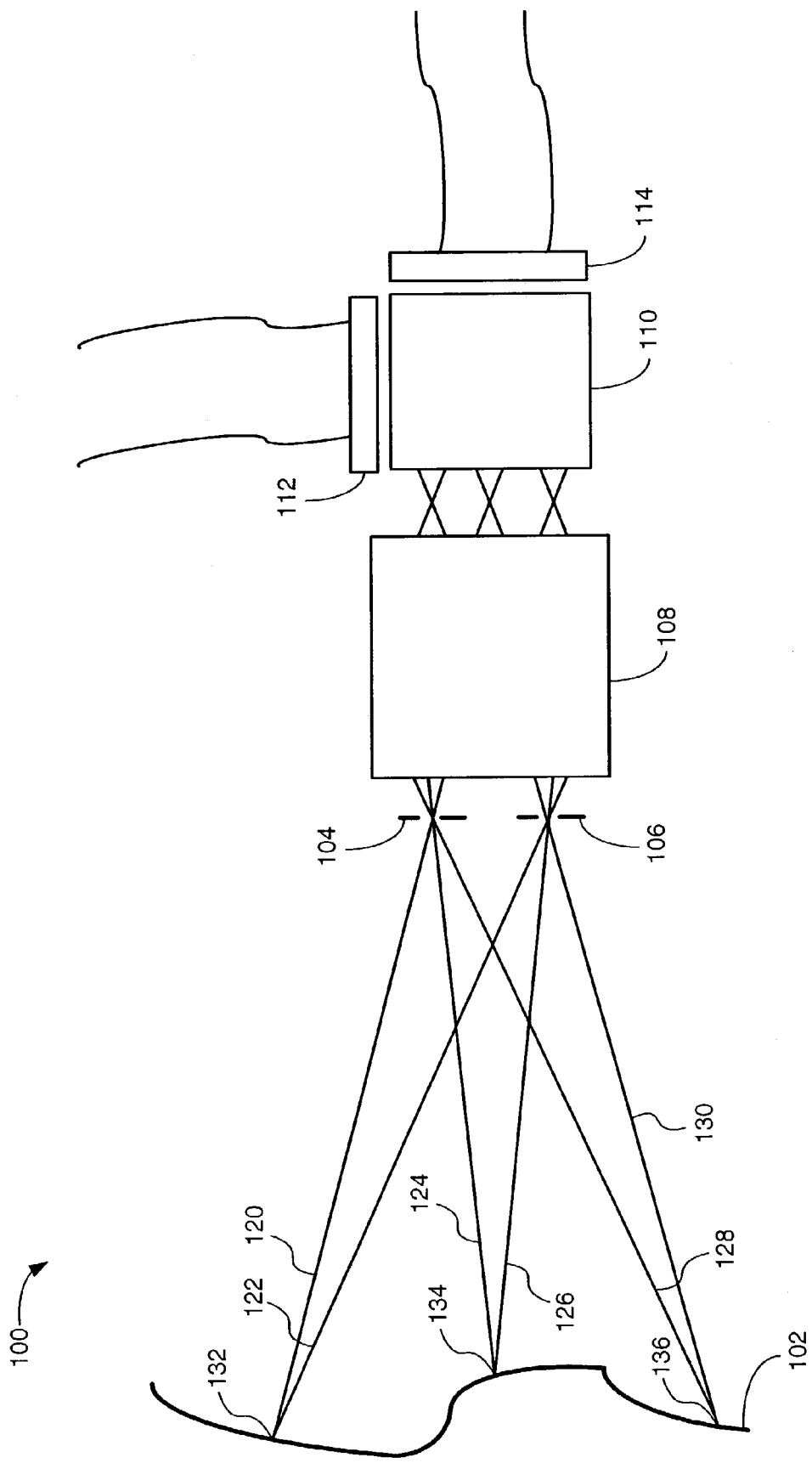
FIG. 1 is a schematic illustration of a stereoscopic device, constructed and operative in accordance with an embodiment of the disclosed technique, and an inspected three-dimensional object.

The disclosed technique overcomes the disadvantages of the prior art by providing a common optical imaging assembly for two stereoscopic images and a directional image separator with a directionally selective surface, reflecting rays from a first direction toward a first image detector and transmitting rays from a second direction toward a second image detector. Reference is now made to FIG. 1, which is a schematic illustration of a stereoscopic device, generally referenced 100, constructed and operative in accordance with an embodiment of the disclosed technique, and an inspected three-dimensional object 102. System 100 includes right 104 and left 106 entrance pupils, common optical imaging assembly 108, a directional image separator 110 and image detectors 112 and 114.

Light ray 120, arriving from a first point 132 on three-dimensional object 102, passes through right pupil 104 and further through optical imaging assembly 108, reaching image detector 112. Light ray 122, arriving from first point 132, passes through left pupil 106 and further through optical imaging assembly 108, reaching image detector 114.

Light ray 124, arriving from a second point 134 on three-dimensional object 102, passes through right pupil 104 and further through optical imaging assembly 108, reaching image detector 112. Light ray 126, arriving from second point 134, passes through left pupil 106 and further through optical imaging assembly 108, reaching image detector 114.

Light ray 128, arriving from a third point 136 on three-dimensional object 102, passes through right pupil 104 and further through optical imaging assembly 108, reaching image detector 112. Light ray 130, arriving from third point 136, passes through left pupil 106 and further through optical imaging assembly 108, reaching image detector 114.

Figure 2:
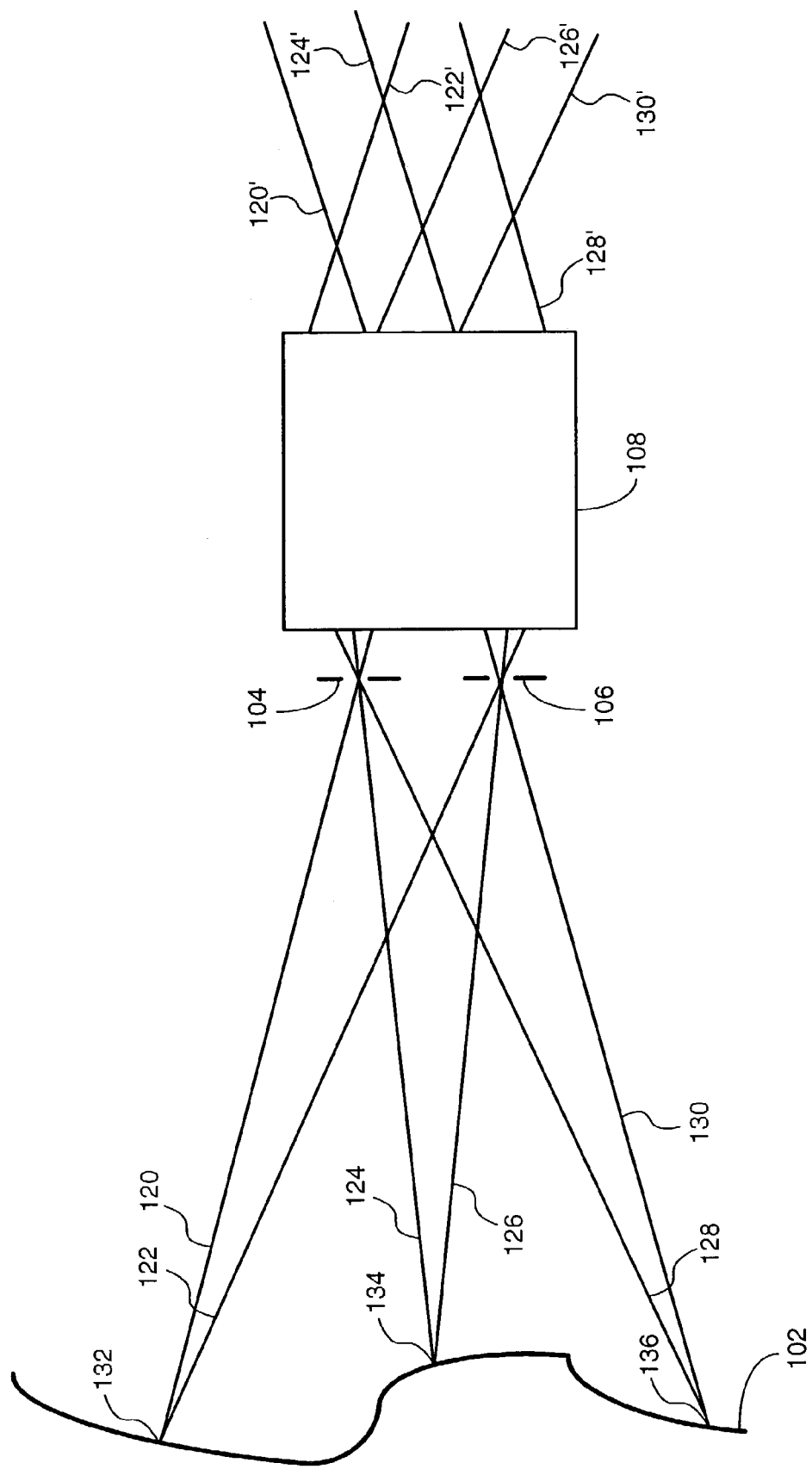
FIG. 2 is an illustration in detail of the common optical imaging assembly and the three-dimensional object of FIG. 1.

Reference is now made to FIG. 2, which is an illustration in detail of common optical imaging assembly 108 (FIG. 1) and the three-dimensional object 102. Common optical imaging assembly 108 transforms the directions of rays, according to the entrance pupils through which they enter.

Light rays 120, 124 and 128 enter common imaging assembly 108 through right pupil 104, and exit common imaging assembly 108 as light rays 120', 124' and 128', respectively. Light rays 122, 126 and 130 enter common imaging assembly 108 through left pupil 106, and exit common imaging assembly 108 as light rays 122', 126' and 130', respectively.

Figure 3:
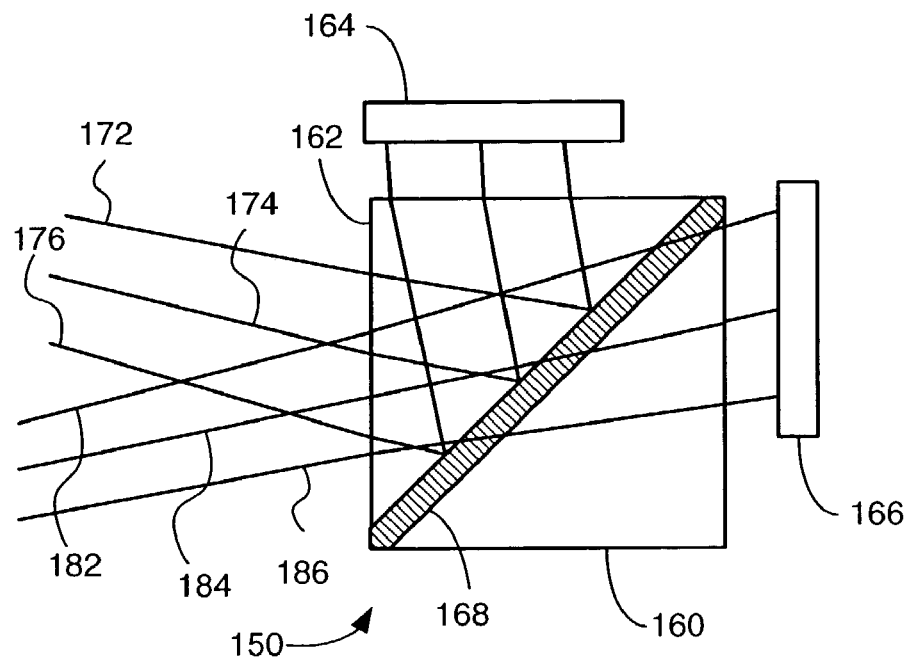
FIG. 3 is a schematic illustration of a directional image separator, constructed and operative in accordance with another embodiment of the disclosed technique.
Figure 4:
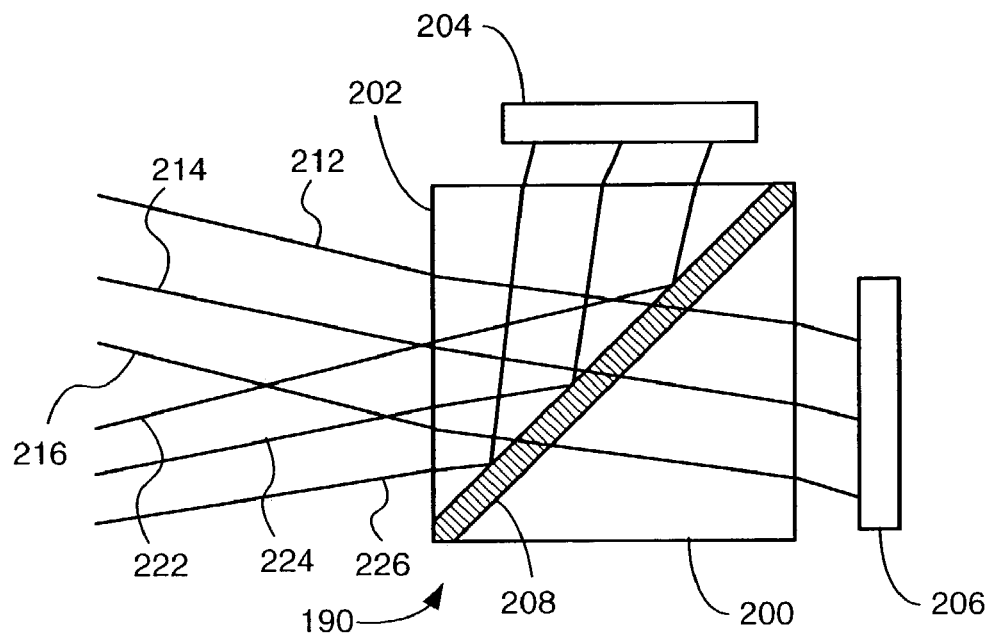
FIG. 4 is a schematic illustration of a directional image separator, constructed and operative in accordance with a further embodiment of the disclosed technique.

Reference is now made to FIG. 3, which is a schematic illustration of a directional image separator, generally referenced 150, constructed and operative in accordance with another embodiment of the disclosed technique, and image detectors 164 and 166. Directional image separator 150 can be incorporated as image separator 110 in a stereoscopic device such as device 100 (FIG. 1). Directional image separator 150 includes prisms 160 and 162, and an optical layer 168.

The operation of image separator 150 is based on optical layers whose coefficient of reflection depends on the angle of incidence. The boundary between optical layer 168 and prism 162 operates as a directionally selective surface. Optical layer 168 reflects light arriving from a first range of directions, and transmits light arriving from a second range of directions. In the present example, optical layer 168 is a portion of dielectric material. It is noted that optical layer 168 may include a plurality of dielectric layers. Alternatively, optical layer 168 may include another type of directionally selective material such as a holographic material, a lattice, and the like. It is noted that prisms 160 and 162 may generally be solid or fluid.

Light rays 172, 174 and 176 arrive at prism 162 from the common imaging optical assembly (not shown), having passed through a first pupil (not shown). Light rays 172, 174 and 176 pass through prism 162 and arrive at optical layer 168. Light rays 172, 174 and 176 form small angles of incidence relative to optical layer 168. Optical layer 168 reflects light rays 172, 174 and 176 back through prism 162, to image detector 164.

Light rays 182, 184 and 186 arrive at optical layer 168 from the common imaging optical assembly (not shown), having passed through a second pupil (not shown). Light rays 182, 184 and 186 pass through prism 162 and arrive at optical layer 168. Light rays 182, 184 and 186 form larger angles of incidence relative to optical layer 168, than light beams 172, 174 and 176. Optical layer 168 transmits light rays 182, 184 and 186 through prism 160, toward image detector 166. Prism 160 completes the optical path of light rays 182, 184 and 186. Thus, the optical paths of the reflected and refracted light rays can be made substantially equal, whereby image detectors 164 and 166 receive confocal images.

Optical layer 208 has different optical properties than optical layer 168 (FIG. 3). The boundary between optical layer 208 and prism 202 operates as a directionally selective surface, having different properties than the directionally selective surface of directional image separator 150 (FIG. 3).

Light rays 212, 214 and 216 arrive at prism 202 from the common imaging optical assembly (not shown), having passed through a first pupil (not shown). Light rays 212, 214 and 216 pass through prism 202 and arrive at optical layer 208. Light rays 212, 214 and 216 form small angles of incidence relative to optical layer 208. Optical layer 208 transmits light rays 212, 214 and 216 through prism 200, toward image detector 206.

Light rays 222, 224 and 226 arrive at prism 202 from the common imaging optical assembly (not shown), having passed through a second pupil (not shown). Light rays 222, 224 and 226 pass through prism 202 and arrive at optical layer 208. Light rays 222, 224 and 226 form larger angles of incidence relative to optical layer 208 (i.e., beyond the critical angle), than light beams 212, 214 and 216. Optical layer 208 reflects light rays 222, 224 and 226 back through prism 202, toward image detector 204.

Figure 5:
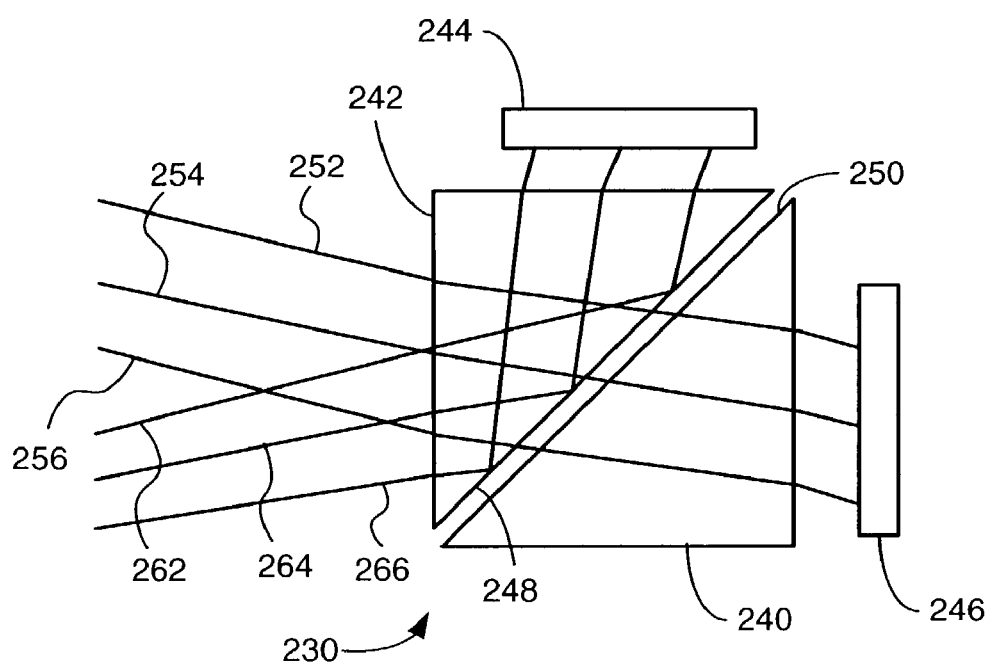
FIG. 5 is a schematic illustration of a directional image separator, constructed and operative in accordance with another embodiment of the disclosed technique.

Reference is now made to FIG. 5, which is a schematic illustration of a directional image separator, generally referenced 230, constructed and operative in accordance with a further embodiment of the disclosed technique, and image detectors 244 and 246. Directional image separator 230 includes prisms 240 and 242. Prisms 240 and 242 include hypotenuse surfaces 250 and 248, respectively. Surfaces 248 and 250 are substantially parallel and placed in close proximity there between.

The operation of image separator 230 is based on the Total Internal Reflection (TIR) principle. Surface 248 operates as a directionally selective surface. Surface 248 reflects light arriving from a first range of directions, and transmits light arriving from a second range of directions. Light rays 252, 254 and 256 arrive at prism 242 from the common imaging optical assembly (not shown), having passed through a first pupil (not shown). Light rays 252, 254 and 256 pass through prism 242 toward surface 248. Light rays 252, 254 and 256 form angles of incidence relative to surface 248, which are smaller than the angle of incidence required for TIR. Thus, light rays 252, 254 and 256 are transmitted through surface 248 toward prism 240. Light rays 252, 254 and 256 pass through prism 240 toward image detector 246.

Light rays 262, 264 and 266 arrive at prism 242 from the common imaging assembly (not shown), having passed through a second pupil (not shown). Light rays 262, 264 and 266 pass through prism 242 and arrive at surface 248. Light rays 262, 264 and 266 form angles of incidence relative to surface 248, which are larger than the angle of incidence required for TIR. Thus, surface 248 reflects light rays 262, 264 and 266 back through prism 242, toward image detector 244.

It will be appreciated by persons skilled in the art that the disclosed technique is not limited to what has been particularly shown and described hereinabove. Rather the scope of the disclosed technique is defined only by the claims, which follow.

The invention claimed is:

1. Stereoscopic device comprising:
   a first entrance pupil, receiving a first image of at least one object;
   a second entrance pupil, receiving a second image of said at least one object;
   a directional image separator, receiving said first image from said first entrance pupil and receiving said second image from said second entrance pupil;
   a common optical imaging assembly, located between said entrance pupils and said directional image separator, conveying said first image from said first entrance pupil to said directional image separator, conveying said second image from said second entrance pupil to said directional image separator, providing said first image to said directional image separator in a first source direction, and providing said second image to said directional image separator in a second source direction;
   a first image detector; and
   a second image detector,
   wherein said directional image separator comprises a directionally selective surface, said directionally selective surface reflecting said first image in a first target direction, towards said first image detector, and transmitting said second image in a second target direction, towards said second image detector, and
   wherein said first image and said second image are at least partially overlapping, when arriving at said directionally selective surface.

2. The stereoscopic device according to claim 1, wherein said directional image separator comprises at least one prism, said at least one prism comprising a plurality of prism surfaces,
   wherein at least one of said prism surfaces is an entrance surface, for receiving said first and second images,
   wherein said at least one prism surface defines said directionally selective surface,
   wherein said at least one prism surface is an exit surface, for transmitting said first image toward said first image detector, and
   wherein at least another one of said prism surfaces is another exit surface, for reflecting said second image toward said second image detector.

3. The stereoscopic device according to claim 1, wherein said directional image separator comprises a portion of dielectric material, said portion of dielectric material comprising at least one surface, defining said directionally selective surface.

4. The stereoscopic device according to claim 1, wherein said directional image separator further comprises a prism, wherein said prism comprises at least a first surface, for receiving said second image from said directionally selective surface, and a second surface, for transmitting said second image towards said second image detector.

5. The stereoscopic device according to claim 1, wherein at least one of said first image detector and said second image detector comprises a two-dimensional image sensor array.

6. The stereoscopic device according to claim 5, said first image detector comprising a first and said second image detector comprises a two-dimensional image sensor array, said first two-dimensional image sensor array and said second two-dimensional image sensor array oriented substantially orthogonal there between.

7. The stereoscopic device according to claim 6, wherein one of said first said first two-dimensional image sensor array and said second two-dimensional image sensor array is substantially perpendicular to the optical axis of said common optical imaging assembly.

8. The stereoscopic device according to claim 1, wherein said first entrance pupil, said second entrance pupil, said directional image separator, said common optical imaging assembly, said first image detector and said second image detector are located within an endoscope.

9. Method for producing a stereoscopic image, the method comprising the procedures of:
   receiving a first image through a first entrance pupil;
   receiving a second image through a second entrance pupil;
   conveying said first image through a common optical assembly from said first entrance pupil to a directional image separator and providing said first image to said directional image separator in a first source direction;
   conveying said second image through said common optical assembly from said second entrance pupil to said directional image separator and providing said second image to said directional image separator in a second source direction;
   reflecting said first image, at a directionally selective surface, in a first target direction, towards a first image detector; and
   transmitting said second image, at said directionally selective surface, in a second target direction, towards a second image detector,
   wherein said first image and said second image are at least partially overlapping, when arriving at said directionally selective surface.

10. The method according to claim 9, further comprising the procedures of:
    detecting said first image; and
    detecting said second image.

* * * * *